United States Patent [19]

Hartung, deceased et al.

[11] Patent Number: 4,885,418

[45] Date of Patent: Dec. 5, 1989

[54] PROCESS FOR REMOVING METAL HALIDES FROM LIQUID ORGANIC WATER-IMMISCIBLE SUBSTANCES

[75] Inventors: Sigurd Hartung, deceased, late of Cologne, by Erika Hartung, Volker Hartung, Dirk Hartung, heirs; by Birgit Hartung-Merse, heir, Pulheim-Sinnersdorf; Uwe Beck, Leverkusen; Ulrich Kappler, Langenfeld; Alfred Mitschker, Odenthal-Holz; Andreas Gräfe, Leverkusen, all of Fed. Rep. of Germany

[73] Assignee: Bayer Aktiengesellschaft, Leverkusen, Fed. Rep. of Germany

[21] Appl. No.: 242,402

[22] Filed: Sep. 9, 1988

[30] Foreign Application Priority Data

Sep. 23, 1987 [DE] Fed. Rep. of Germany ....... 3731995

[51] Int. Cl.$^4$ .............................................. C07C 17/38
[52] U.S. Cl. ..................................................... 570/211
[58] Field of Search ............................... 570/211, 264

[56] References Cited

FOREIGN PATENT DOCUMENTS

| 0124866 | 3/1979 | Fed. Rep. of Germany ...... 570/211 |
| 0650984 | 3/1979 | U.S.S.R. .............................. 570/211 |
| 1359881 | 7/1974 | United Kingdom ................ 570/211 |

*Primary Examiner*—Werren B. Lone
*Attorney, Agent, or Firm*—Sprung Horn Kramer & Woods

[57] ABSTRACT

According to the invention, metal halides are removed from liquid organic water-immiscible substances by treating the liquid organic water-immiscible substances which contain the metal halides with a water-containing anion-exchanger in the OH form.

8 Claims, No Drawings

PROCESS FOR REMOVING METAL HALIDES FROM LIQUID ORGANIC WATER-IMMISCIBLE SUBSTANCES

The invention relates to a process for removing metal halides from liquid organic water-immiscible substances.

In the preparation of organic compounds, frequently solutions or mixtures of organic compounds or even individual organic water-immiscible compounds are formed which still contain small amounts of metal halides, for example $AlCl_3$, $TiCl_4$, $SnCl_4$, $ZnCl_2$, $MnCl_2$, $MoCl_3$, $SbCl_3$, $SbCl_5$, $ZrCl_4$ or $FeCl_3$ ($Br_3$) and have to be freed from these metal halides.

For example, in the chlorination of organic compounds such as benzene, toluene, nitrobenzene or naphthalene in the presence of iron halides, for example of Fe (III) chloride, chlorination mixtures containing iron halides are formed. The desired pure compounds have to be, in most cases, recovered from these mixtures by fractional distillation. However, before the distillation the iron halides must be completely removed from the mixtures because they interfere in the distillation workup; they lead to cloggings and corrosion in the distillation columns.

The processes employed up to now for removing iron halides from chlorination mixtures, washing of the chlorination mixtures with water or addition of dry sodium carbonate to the mixtures, have the disadvantage that they form substantial amounts of waste water or solid waste products which are often difficult to filter.

It has now been found that the iron halides can be removed from the chlorination mixtures in a simple manner without the formation of waste water and/or waste products, if these mixtures are treated with water-containing anion-exchangers.

Surprisingly, it has been found that water-containing anion-exchangers not only bind halide but also iron ions. It has been found that the iron ions are not bound, as was to be expected according to the prior art for the adsorption of metal ions by ion-exchangers, by strongly acidic cation-exchangers but, surprisingly, by anion-exchangers, if these exchangers have a certain water content.

Included in the prior art for the adsorption of ions from aqueous solutions or organic solvents by means of ion-exchangers is the fact that cations, for example metal ions, are bound by cation-exchangers, and anions, for example metal ions present in the form of anion complexes, are bound by anion-exchangers (see Ullmann's Encyclopaedia of Industrial Chemistry, 4th ed. vol. 13, p. 279-346 and Industrial and Engineering Chemistry vol. 45, p. 2577-2580 (1953)). Since iron is however not present in the form of an anion complex in the chlorination mixtures—the hydrogen chloride formed in the chlorination is removed by purging the chlorination mixture—there was no reason for the assumption that the iron ions in the case where they could not be removed by a cation-exchanger could now be bound by an anion-exchanger.

Furthermore, it has been found that anion-exchangers containing a certain amount of water are not only suitable for removing iron halides such as iron chloride and iron bromide from chlorination mixtures but very generally for removing metal halides such as the metal halides $FeCl_3$, $FeBr_3$, $AlCl_3$, $TiCl_4$, $SnCl_4$, $ZnCl_2$, $SbCl_3$, $SbCl_5$, $MnCl_2$, $MoCl_3$, $ZrCl_4$ which are used as chlorination catalysts from liquid organic water-immiscible substances.

The invention therefore relates to a process for removing metal halides, preferably metal halides used as chlorination catalysts, in particular iron halides, from liquid organic water-immiscible substances; the process is characterized in that the liquid organic water-immiscible substances which contain the metal halides are treated with water-containing anion-exchangers.

For economic reasons, the process is particularly suitable for removing small amounts of metal halide, for example amounts <200 ppm.

The water content of the anion-exchangers should be 40 to 80% by weight, preferably 50 to 70% by weight, based on the total weight of the moist anion-exchanger.

The anion-exchangers used can basically be all known types of anion-exchanger, that is macroporous and gel-like, strongly basic and weakly basic anion exchangers having a matrix consisting of crosslinked polystyrene or having a matrix consisting of crosslinked polyacrylate. However, macroporous anion-exchangers having a matrix consisting of crosslinked polystyrene have proved particularly effective. These anion-exchangers can be strongly or weakly basic.

The anion-exchangers are used in their OH form.

The process according to the invention is preferably carried out in such a manner that the liquid organic water-immiscible substance which is to be freed of metal halide is passed through the anion-exchanger arranged in a suitable apparatus. A suitable apparatus is, for example, a filter tube which is equipped on one or both ends with a bottom which is permeable to liquids and impermeable to anion-exchangers. The specific charge at which the liquid organic substance is filtered through the anion-exchanger should be about 2 to 10 bed volumes (BV)/h $$\left( BV = \frac{m^3 \text{ of liquid}}{m^3 \text{ of anion-exchanger}} \right).$$

The organic compound to be purified is passed through the anion-exchanger until the concentration of the metal ions and halide ions in the liquid substance running off the anion-exchanger has risen to the value previously determined as the limiting value.

After reaching the previously determined limiting value in the run-off from the anion-exchanger, the passage of the liquid organic substance to be purified through the anion-exchanger is stopped. The consumed anion-exchanger can subsequently be used again after treatment with dilute aqueous hydrochloric acid, for example 20% strength hydrochloric acid, and regeneration in a manner known per se with 2-10% strength sodium hydroxide solution.

The liquid organic water-immiscible substances to be treated according to the invention do not have to be liquid at room temperature, instead it is sufficient if they are liquid at temperatures below 100° C., because the adsorption of metal halides from the organic substances is not impaired by elevated temperatures.

The treatment according to the invention of the liquid organic water-immiscible substances can be carried out both at room temperature and also at elevated temperatures from 20 to 100° C. The treatment temperature is dependent on the temperature at which the organic substance is present in liquid form, but it is also dependent on the temperature at which the organic substance to be treated is formed and whether and, if it does, at which temperature it is intended for it to be processed further after the removal of the metal halide. The chlorination mixture obtained in the chlorination of toluene in the presence of iron(III) chloride or bromide and freed from dissolved hydrogen chloride by purging with air has a temperature of about 55° C. Without having to be cooled, it can be passed directly through the anion-exchanger and subsequently be distilled directly. This method avoids unnecessary energy losses, such as inevitably occur if the chlorination mixture is cooled to room temperature and the mixture heated again to the distillation temperature.

Liquid organic water-immiscible substances which can be used in the process according to the invention and which may be mentioned as examples are:

Aromatic hydrocarbons such as benzene, toluene, xylene, ethylbenzene and naphthalene; chlorinated aromatic hydrocarbons such as chlorobenzene, dichlorobenzene, polychlorobenzenes; aliphatic hydrocarbons such as heptane, cyclohexane; chlorinated aliphatic hydrocarbons such as chloroform, tetrachloromethane, dichloroethane; nitrated aromatic hydrocarbons such as nitrobenzene or nitrotoluenes; nitrated aliphatic hydrocarbons such as nitromethane; chlorinated nitrated aromatic hydrocarbons such as nitrochlorobenzenes and nitrochlorotoluenes.

Liquid organic water-immiscible substances which are preferably used in the process according to the invention are chlorination mixtures, such as are formed in the chlorination of benzene, chlorobenzene, toluene, chlorotoluene, benzoyl chloride and naphthalene in the presence of iron(III) chloride and/or iron(III) bromide. These chlorination mixtures are first largely freed from hydrogen chloride dissolved therein by purging with air or nitrogen before they are freed from iron halide in the process according to the invention.

EXAMPLE 1

A chlorination mixture obtained in the chlorination of toluene in the presence of iron(III) chloride as catalyst and subsequently freed from dissolved hydrogen chloride by 10 hours of purging with air (composition of the mixture: 60% by weight of toluene, 20.5% by weight of o-chlorotoluene, 0.3% by weight of m-chlorotoluene, 18.7% by weight of p-chlorotoluene, 0.4% by weight of dichlorotoluenes; $Fe^{3+}$ content: 173 ppm, $Cl^-$: 350 ppm) is passed at a specific charge of 4 bed volumes (BV)/h from top to bottom through 500 ml of a macroporous, medium-basic, water-moist anion-exchanger based on polystyrene crosslinked with 6% by weight of divinylbenzene (total capacity of basic groups: 1.5 mol/l, 0.3 mol/l thereof strongly basic groups; water content: 60% by weight) which anion-exchanger is present in a filter tube (diameter: 45 mm) arranged in a vertical position. During the passage, the anion-exchanger is covered by the chlorination mixture.

The iron and chloride ion contents of the chlorination mixture running off from the anion-exchanger are: $Fe^{3+}$: <1 ppm; $Cl^-$: <32 ppm.

After a throughput of 79 l, the iron chloride content in the run-off of the anion-exchanger increases noticeably and the anion-exchanger is exhausted. No further mixture is passed through, and the anion-exchanger is first treated with 20% strength aqueous hydrochloric acid and then regenerated in a conventional manner with dilute sodium hydroxide solution (2-10% strength).

Virtually the same result ($Fe^{3+}$ and $Cl^-$ contents of the chlorination mixture running off from the anion-exchanger and throughput until the anion-exchanger is exhausted) was obtained as the chlorination mixture being passed through the anion-exchanger has a temperature of 55° C.

EXAMPLE 2

The procedure was carried out as described in Example 1 except that a chlorination mixture was used which contained only 82 ppm of $Fe^{3+}$ and 160 ppm of $Cl^-$.

The iron and chloride ion contents of the chlorination mixture running off from the anion-exchanger was: $Fe^{3+}$: 1 ppm; $Cl^-$: 25 ppm.

After 192 l of chlorination mixture have been passed through, the anion-exchanger was exhausted.

EXAMPLE 3

The chlorination mixture described in Example 1 is passed through 500 ml of a macroporous weakly basic water-moist anion-exchanger (matrix: polystyrene crosslinked with 8% of divinylbenzene; total capacity of basic groups: 2.0 equivalents/l; water content 50% by weight) at a specific charge of 4 BV/h.

The iron and chloride ion contents of the chlorination mixture before the treatment with the anion-exchanger: $Fe^{3+}$: 75 ppm; $Cl^-$: 150 ppm.

The iron and chloride ion contents of the chlorination mixture running off from the anion-exchanger: $Fe^{3+}$: 1 ppm; $Cl^-$: 51 ppm.

After 212 l of chlorination mixture have been passed through, the anion-exchanger is exhausted.

EXAMPLE 4

The procedure is carried out as described in Example 1 except that a different chlorination mixture is used (composition of the chlorination mixture: 35% by weight of o-chlorotoluene, 19.2% by weight of 2,5-dichlorotoluene, 16.9% by weight of 2,6-dichlorotoluene, 11.1% by weight of 2,4-dichlorotoluene, 8.3% by weight of 2,3-dichlorotoluene, 10.3% by weight of trichloro-toluenes; the iron and chloride ion contents of the mixture: $Fe^{3+}$: 12 ppm; $Cl^-$: 25 ppm). The chlorination mixture is passed through the anion-exchanger at a specific charge of 2 BV/h.

The iron and chloride ion contents of the chlorination mixture flowing off from the anion-exchanger are: $Fe^{3+}$: <1 ppm; $Cl^-$: 21 10 ppm.

After 458 l of chlorination mixture have been passed through, the anion-exchanger is exhausted.

EXAMPLE 5

A chlorination mixture obtained in the chlorination of naphthalene in the presence of Fe(III) chloride as a catalyst (composition of the mixture: 30% by weight of naphthalene, 65% by weight of monochloronaphthalene, 5% by weight of dichloronaphthalene), is passed at a temperature of 60° C. from top to bottom through 500 ml of a macroporous weakly basic, water-moist anion-exchanger (matrix:polystyrene crosslinked with 8% of divinylbenzene; total capacity of basic groups: at least 1.8 equivalents/l, water content: 45–55% by weight) at a specific gharge of 4 BV/h; the anion-exchanger is present in a vertical position arranged filter tube (diameter: 45 mm).

The iron and chloride ion contents of the chlorination mixture before the treatment: $Fe^{3+}$: 280 ppm; $Cl^-$: 550 ppm; the iron and chloride ion contents of the chlorination mixture running off from the anion-exchanger: $Fe^{3+}$: 40 ppm; $Cl^-$: 100 ppm.

After 50 l of chlorination mixture have been passed through, the anion-exchanger is exhausted.

What is claimed is:

1. A process for removing metal halides from a liquid organic water-immiscible hydrocarbon chlorination mixture, which comprises treating the liquid organic water-immiscible mixture which contains the metal halides with a water-containing anion-exchanger in the OH form.

2. The process of claim 1, wherein the water-containing anion-exchanger contains 40 to 80% by weight of water, based on the weight of the water-moist anion-exchanger.

3. The process of claim 1, wherein the anion-exchanger is a macroporous, strongly or weakly basic anion-exchanger based on crosslinked polystyrene.

4. The process of claim 1 wherein the organic water-immiscible mixture is a chlorination product formed in the chlorination of aromatic hydrocarbons in the presence of a metal halide chlorination catalyst.

5. The process of claim 1, wherein the metal halide is an iron halide.

6. The process of claim 1, wherein the metal halide is iron(III) chloride or iron(III) bromide.

7. The process of claim 4, wherein the metal halide is an iron halide.

8. The process of claim 1, wherein the treating is carried at between room temperature and 100° C.

* * * * *